United States Patent
Johannison

(10) Patent No.: US 8,998,865 B2
(45) Date of Patent: Apr. 7, 2015

(54) APPARATUS AND METHOD FOR CONTROLLING THE NEGATIVE PRESSURE IN A WOUND

(75) Inventor: Ulf Johannison, Landvetter (SE)

(73) Assignee: Mölnlycke Health Care AB, Göteborg (SE)

( * ) Notice: Subject to any disclaimer, the term of this patent is extended or adjusted under 35 U.S.C. 154(b) by 616 days.

(21) Appl. No.: 13/266,959

(22) PCT Filed: Apr. 29, 2010

(86) PCT No.: PCT/SE2010/050472
§ 371 (c)(1),
(2), (4) Date: Oct. 28, 2011

(87) PCT Pub. No.: WO2010/126444
PCT Pub. Date: Nov. 4, 2010

(65) Prior Publication Data
US 2012/0046625 A1  Feb. 23, 2012

(30) Foreign Application Priority Data
Apr. 30, 2009 (SE) ........................ 0950291

(51) Int. Cl.
*A61M 1/00* (2006.01)
(52) U.S. Cl.
CPC .......... *A61M 1/0031* (2013.01); *A61M 1/0001* (2013.01); *A61M 1/0037* (2013.01); *A61M 1/0088* (2013.01)
(58) Field of Classification Search
CPC .................. A61F 13/8405; A61F 2013/00174; A61F 2013/00536; A61F 2013/0091; A61L 15/46; A61L 2300/404; A61M 1/0005; A61M 1/001; A61M 1/0013; A61M 1/0023; A61M 1/0088; A61M 27/00; A61M 2001/0017; A61M 2001/0052
USPC .................................. 604/304, 305, 313, 319
See application file for complete search history.

(56) References Cited

U.S. PATENT DOCUMENTS

| | | | |
|---|---|---|---|
| 3,572,340 A | 3/1971 | Lloyd | 128/278 |
| 3,742,952 A | 7/1973 | Magers | 128/278 |
| 4,382,441 A | 5/1983 | Svedman | 604/291 |
| 4,525,166 A | 6/1985 | Leclerc | 604/133 |

(Continued)

FOREIGN PATENT DOCUMENTS

| | | |
|---|---|---|
| CN | 101208115 A | 6/2008 |
| EP | 0865304 | 7/2002 |

(Continued)

OTHER PUBLICATIONS

Chariker, et al. "Effective Management of Incisional and Cutaneous Fistulae with Closed Suction Wound Drainage." Journal of Contemp. Surg., Jun. 1989, vol. 34, pp. 59-63.

(Continued)

*Primary Examiner* — Melanie Hand
(74) *Attorney, Agent, or Firm* — Ballard Spahr LLP

(57) ABSTRACT

An apparatus is disclosed for treating a wound with negative pressure. The apparatus includes a wound cover, a first pump for providing said negative pressure to the wound, a canister, a first conduit between the wound cover and the canister, a means for measuring the pressure within the canister, and a second conduit which connects the canister with the first pump. A method for controlling the negative pressure in a wound using such an apparatus is also disclosed.

16 Claims, 2 Drawing Sheets

(56) References Cited

U.S. PATENT DOCUMENTS

| | | | |
|---|---|---|---|
| 4,969,880 A | 11/1990 | Zamierowski | 604/305 |
| 5,358,494 A | 10/1994 | Svedman | 604/313 |
| 5,636,643 A | 6/1997 | Argenta | 128/898 |
| 5,645,081 A | 7/1997 | Argenta | 128/898 |
| 5,971,714 A | 10/1999 | Schaffer et al. | 417/44.2 |
| 6,855,135 B2 | 2/2005 | Lockwood | 604/313 |
| 7,438,705 B2 | 10/2008 | Karpowicz et al. | 604/313 |
| 7,503,910 B2 | 3/2009 | Adahan | 604/319 |
| 7,779,625 B2 | 8/2010 | Joshi | 60/313 |
| 2007/0265586 A1 | 11/2007 | Joshi | 60/313 |
| 2009/0030383 A1 | 1/2009 | Larsen | 604/315 |
| 2009/0036754 A1 | 2/2009 | Pons et al. | 600/561 |
| 2009/0036873 A1 | 2/2009 | Nielsen | 604/315 |
| 2009/0326488 A1 | 12/2009 | Budig | 604/319 |

FOREIGN PATENT DOCUMENTS

| | | |
|---|---|---|
| WO | WO 2006/025848 | 3/2006 |
| WO | WO 2007/092397 | 8/2007 |
| WO | WO-2008/012278 A1 | 1/2008 |
| WO | WO 2008/039223 | 4/2008 |
| WO | WO 2008/132215 | 11/2008 |
| WO | WO 2008/135997 | 11/2008 |
| WO | WO 2009/002260 | 12/2008 |
| WO | WO 2009/004368 | 1/2009 |
| WO | WO 2009/016195 | 2/2009 |
| WO | WO 2009/016605 | 2/2009 |
| WO | WO 2009/071948 | 6/2009 |
| WO | WO 2009/089390 | 7/2009 |
| WO | WO 2009/114624 | 9/2009 |

OTHER PUBLICATIONS

Davydov, et al. "The Bacteriological and Cytological Assessment of Vacuum Therapy of Purulent Wounds." Vestnik Khirurgii, Oct. 1988, pp. 48-52 (published in English in The Kremlin Papers, Perspectives in Wound Care).

Davydov, et al. "Vacuum Therapy in the Treatment of Purulent Lactation Mastitis." Vestnik Khirurgii, Sep. 1986, pp. 66-70 (published in English in The Kremlin Papers, Perspectives in Wound Care).

Davydov, et al. "Concepts for Clinical Biological Management of the Wound Process in the Treatment of Purulent Wounds using Vacuum Therapy." Vestnik Khirurgii, Feb. 1991, pp. 132-135 (published in English in The Kremlin Papers, Perspectives in Wound Care).

Kostiuchenok, et al. "The Vacuum Effect in the Surgical Treatment of Purulent Wounds." Vestnik Khirurgii, Sep. 1986, pp. 18-21 (published in English in The Kremlin Papers, Perspectives in Wound Care).

Usupov, et al. "Active Wound Draingage." Vestnik Khirurgii, 1987, pp. 42-45 (published in English in The Kremlin Papers, Perspectives in Wound Care).

International Preliminary Report on Patentability issued Nov. 1, 2011 for International Application No. PCT/SE2010/050472, which was filed on Apr. 29, 2009 and which was published on Nov. 4, 2010 as WO/2010/126444 (Inventor—Johannison; Applicant—Molnlycke Health Care AB) (pp. 1-8).

International Search Report and Written Opinion issued Jun. 30, 2010 for International Application No. PCT/SE2010/050472, which was filed on Apr. 29, 2009 and which was published on Nov. 4, 2010 as WO/2010/126444 (Inventor—Johannison; Applicant—Molnlycke Health Care AB) (pp. 1-15).

APPARATUS AND METHOD FOR CONTROLLING THE NEGATIVE PRESSURE IN A WOUND

CROSS REFERENCE TO RELATED APPLICATIONS

The present application is a National Phase Application of International Application No. PCT/SE2010/050472, filed Apr. 29, 2010, which claims priority to Swedish Patent Application No. 0950291-5, filed Apr. 30, 2009, which applications are incorporated herein fully by this reference.

TECHNICAL FIELD

The present invention relates to an apparatus for treating wound with negative pressure, said apparatus including a wound cover, a first pump for providing said negative pressure to the wound, a canister, a first conduit between the wound cover and the canister, which first conduit connects the wound with the canister, means for measuring the pressure within the canister, and a second conduit which connects the canister with the first pump.

The invention also relates to a method for controlling the negative pressure in the wound area with use of an apparatus for treating wound with negative pressure, comprising using a first pump to create a negative pressure within a canister, which is connected with the wound via a first conduit, and measuring the pressure in the canister.

BACKGROUND ART

Healing of wound with negative pressure is today an accepted method for treating difficult and with earlier conventional methods slow-healing wounds.

Drainage of, for example, surgical wounds or other weeping wounds with negative pressure is a standard treatment which has been used for decades. An example of a manual suction pump for this purpose is described in U.S. Pat. No. 3,742,952.

U.S. Pat. No. 3,572,340 describes a pump in the form of an elastically compressible body made of an open-celled foam material, preferably a polyurethane foam, which body also serves as a receptacle for fluid drained from the wound. The pump is said to have a capacity to maintain an negative pressure of 15-80 mmHg for more than 48 hours. A perforated drain is intended to be placed in the wound pocket and is connected to the pump by a tube. A similar device is described in U.S. Pat. No. 4,525,166, in the description of which it is specifically stated that the negative pressure not only drains wound fluid but also draws together the wound edges and stimulates tissue growth and healing of the wound. The two latter publications therefore state that vacuum treatment of wounds stimulates wound healing.

The terms vacuum treatment, treatment with reduced pressure and treatment under negative pressure are used interchangeably in the literature. It should be pointed out that, where these terms are used within this description, treatment at a pressure below normal atmospheric pressure is always meant.

Deep wounds have also been treated with a combination of a rinsing fluid supply and subsequent aspiration. Examples of such devices are described in U.S. Pat. No. 5,358,494 and U.S. Pat. No. 4,382,441.

Extensive studies of the effect of both continuous and intermittent treatment of wounds under negative pressure, i.e. pressure below normal atmospheric pressure, were conducted during the 80's in Russian institutions. It was here demonstrated that slow-healing wounds heal substantially faster with the aid of vacuum treatment compared with conventional treatment methods. It was also shown, inter alia, that treatment with reduced pressure produced a significant antibacterial effect. The said Russian studies are described in articles in the Russian medical journal Vestnik Khirurgii. The articles from the said journal are:
1) Kostiuchenok et al, September 1986, pages 18-21.
2) Davydov et al, September 1986, pages 66-70.
3) Usupov et al, April 1987, pages 42-45.
4) Davydov et al, October 1988, pages 48-52.
5) Davydov et al, February 1991, pages 132-135.

In an article by Chariker et al in the journal Contemporary Surgery, issue 34, June 1989, it is stated that vacuum treatment improves the growth of granulation tissue and the wound contraction of wounds which with conventional treatment are very slow-healing.

Vacuum treatment of wounds is described in for instance U.S. Pat. No. 4,969,880, U.S. Pat. No. 5,645,081, U.S. Pat. No. 5,636,643, U.S. Pat. No. 6,855,135 and WO 2006/025848 A2.

In order to get a good wound healing when using negative pressure treatment it is important to control the pressure at the wound, i.e. that the chosen and set pressure of the system is the same as is achieved at the wound.

The therapy pressure, i.e. the pressure at the wound, is affected by several factors, such as the difference of the height levels of the wound and of the canister when there is a liquid column in the suction tube between the wound and the canister. The tube can also be clogged by exudates with high viscosity.

EP 0 865 304 B1 describes an apparatus that in addition to a drainage conduit between the wound cover and the canister includes an additional conduit connecting the wound cover to a pressure detecting means, whereby the pressure substantially at the wound site can be measured. The apparatus according to EP 0 865 304 B1 describes an embodiment which includes a relief valve for admitting ambient air to the wound site via the additional conduit and means for controlling the operation of said relief valve.

SUMMARY OF THE INVENTION

By means of the present invention an improved device of the type mentioned in the introduction has been achieved. The apparatus in accordance with the invention is characterized in that a circulating pump is arranged to transport gas from the canister to the wound area via a third conduit and back to the canister via the first conduit in order to press out a possible liquid column from the first conduit to the canister.

One advantage with the above defined apparatus is that consumption of energy is much less when gas is circulated in the system instead of letting in ambient air. When ambient air at atmospheric pressure has been let in it is necessary to again establish therapy pressure which demands a lot of energy and quick consumption of batteries.

Another advantage is less discharge of gas from the apparatus and by that the risk is reduced for letting out odour from the apparatus.

According to an embodiment the invention is further characterized in that the circulating pump is arranged to work intermittently.

According to an embodiment the invention is characterized in that said circulation pump is time controlled in order to control the maximal height of a possible liquid column that can be built up in the first conduit during a period when the circulating pump is turned off.

According to an embodiment the invention is characterized in that said means for measuring the pressure within the canister is a pressure sensor.

According to another embodiment the invention is characterized in that a check valve is arranged to hinder gas pumped by the circulating pump from reaching the wound area.

According to another embodiment the invention is characterized in that said check valve is arranged in a connecting branch on the wound cover.

According to an embodiment the invention is characterized in that said wound cover includes a wound filler and a sealing film.

According to an embodiment the invention is characterized in that the apparatus includes a soft adapter which is arranged to connect the wound under the sealing film with the first conduit, and in that said soft adapter includes a soft, flexible tube, which is arranged to be connected to said first conduit.

According to an embodiment the invention is characterized in that said soft, flexible tube comprises an outer impermeable shell of a soft thin plastic film and an open-cell foam enclosed in said shell.

According to a further embodiment the invention is characterized in that means are arranged to analyse the power consumption of the circulating pump and provide an alarm signal when said power consumption indicates that the first conduit and/or the canister is blocked.

According to an embodiment the invention is characterized in that a first filter is arranged in the canister at an outlet to the second conduit and that said filter includes activated carbon.

According to a further embodiment the invention is characterized in that a second filter is arranged in the third conduit to prevent entrance of contaminated gas from the canister to the third conduit.

According to an embodiment the invention is characterized in that a third filter is arranged between the first pump and ambient air.

The method according to the invention is characterized in that gas is transported with a circulating pump from the canister towards the wound region via a third conduit and that said gas is further directed to the first conduit and back through the first conduit to the canister for pushing a possible liquid column of wound exudate reciding in the first conduit to the canister.

The method according to the invention is preferably further characterized in gas is pushed through the third conduit with said circulating pump at regular time intervals and that the length of said time interval is chosen for setting maximal allowed difference of the negative pressure within the wound relatively the set pressure in the canister.

DETAILED DESCRIPTION

Figure 1:
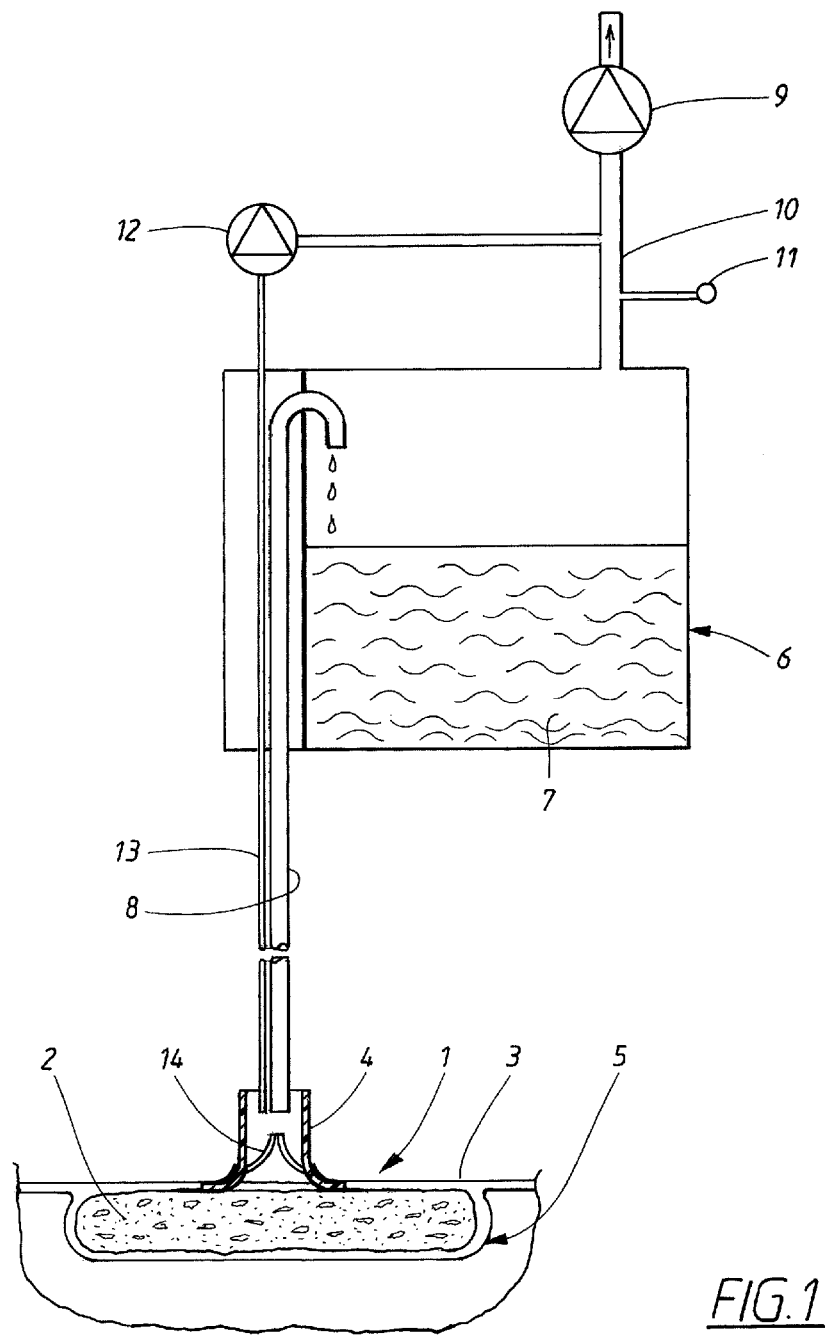
FIG. 1 is a schematic illustration of the apparatus according to the invention.

The apparatus according to the invention includes a wound cover 1, which in the shown embodiment in FIG. 1 comprises a wound filler 2, a sealing film 3 and a connecting branch 4. The wound filler may be open-celled polymeric foam, such as polyurethane foam or polyvinyl alcohol foam having inter-connecting cells for distribution of an applied negative pressure over the wound 5. The sealing film 3 can for example be a polyurethane film.

A canister 6 is arranged to collect wound exudate 7, which is sucked from the wound via a first conduit 8. A first pump 9 is arranged to apply the negative pressure in the canister and in the wound area. The pump 9 is connected with the canister via a second conduit 10. A pressure measuring means 11 is arranged as shown in the second conduit for measuring the pressure within the canister. This pressure is the same as the pressure in the wound area when no wound exudate is present in the first conduit.

The apparatus includes a circulating pump 12 for transporting gas from the canister to the wound area via a third conduit 13 and back to the canister via the first conduit 8 with the purpose to pressing out a possible liquid column from the first conduit to the canister. A check valve 14 is arranged in the connecting branch 4 to hinder gas pumped by the circulating pump 12 from reaching the wound area. The check valve can for instance be a duck bill valve. The check valve 14 is arranged to allow gas and wound exudate to be sucked in the direction from the wound to the canister 6.

The negative pressure in the canister is established with the first pump 9. This negative pressure is transferred to the wound via the first conduit 8. With the expression negative pressure is meant the pressure below atmospheric pressure. A suitable negative pressure is chosen by the care taker, such as a doctor or a nurse. Depending on the type and state of the wound said negative pressure is set at a suitable level, which normally is chosen between about 50-150 mmHg below atmospheric pressure. The pressure in the canister is measured with the pressure detector 11. The pressure in the wound is the same as in the canister when no liquid is blocking the first conduit. If there is a height difference between the wound and the canister and a liquid column is blocking the first conduit the pressure in the wound area differs from the negative pressure in the canister. The effect of a liquid column present in the first conduit is that it will decrease the negative pressure in the wound area. A water column that is one meter high corresponds to a pressure difference of approximately 76 mmHg. This value shall be subtracted from the value in the canister to get the negative pressure in the wound. If it is a negative pressure of 100 mmHg in the canister and the water column is one meter then there is a negative pressure in the wound area of only 24 mmHg.

It is not possible to just compensate for the water column by setting a higher value for the negative pressure in the canister. The reason for that is that it is not possible to know how much exudate there is in the tube or the difference in height between the wound and the canister, which height also can vary when the patient moves for instance from a lying position to a sitting position.

To minimize this problem it is according to the present invention arranged a circulating pump 12 for transporting gas from the canister to the wound region via the third conduit 13 and back to the canister via the first conduit. The gas transported with the circulating pump enters the connecting branch 4 to the wound cover. The check valve 14 hinders the gas from entering the wound area and the gas is forced up through the first conduit 8 and pressing out a possible liquid column from the first conduit to the canister.

An important advantage with the solution according to the invention is that a very small amount of gas is needed for cleaning the first conduit from exudate. One can therefore chose a very small pump as circulating pump. A suitable pump is a small piezoelectric pump, which in use is very quiet and which consume very little power. A further great benefit with the solution according to the invention is that the negative pressure in the canister is hardly affected by said small amount of gas needed for cleaning the first conduit. To achieve and keep the desired negative pressure it is with the solution according to the present invention possible to chose a small pump as the first pump 9. The pump 9 can be powered by batteries, such as rechargeable batteries. In order to control the negative pressure in the canister it is arranged a pressure sensor 11.

The invention will in the following be described in more detail with reference to the embodiment shown in form of a block diagram in FIG. 2.

Figure 2:
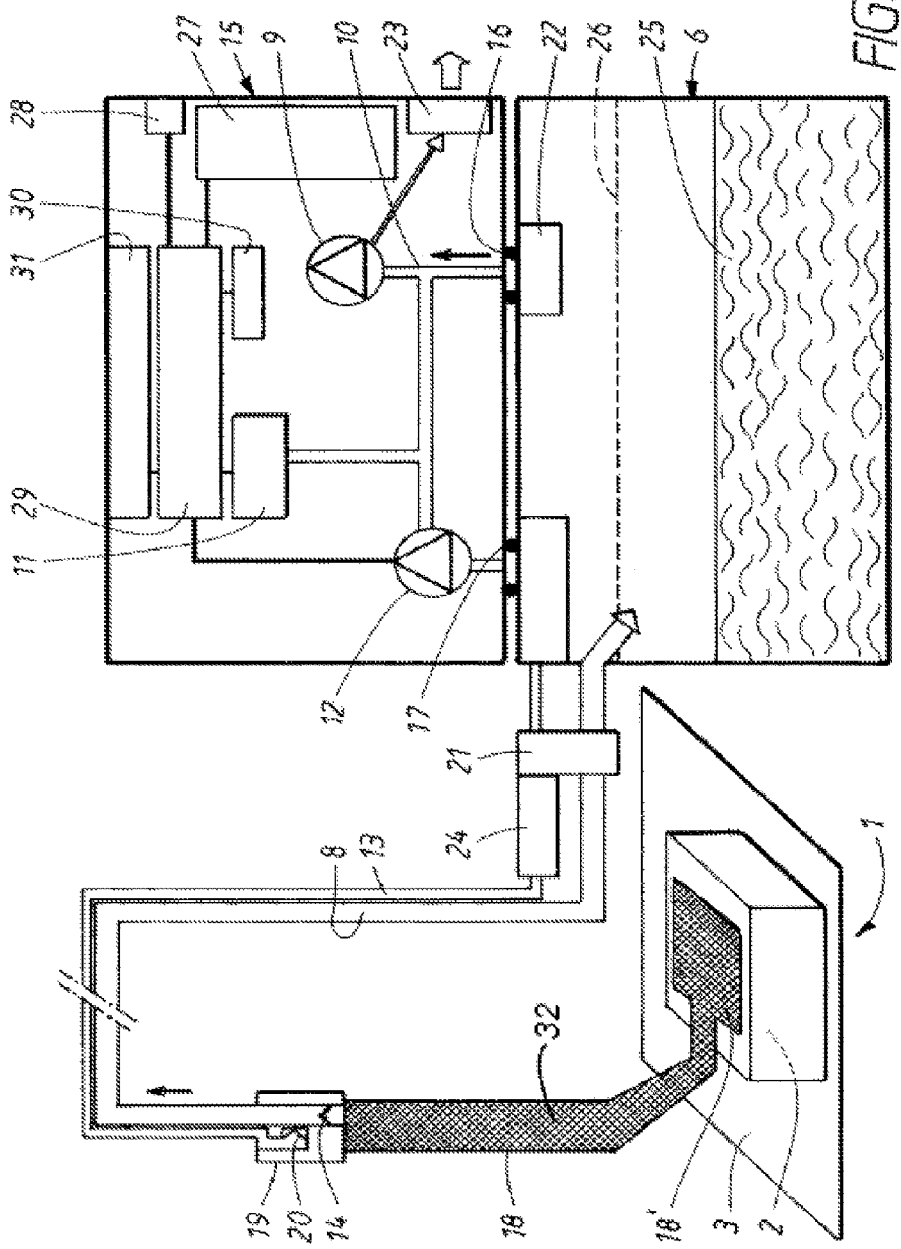
FIG. 2 is a block diagram over a more detailed embodiment of an apparatus according to the invention

Details in FIG. 2 which corresponds to similar details in FIG. 1 have been designated with the same reference number.

The canister 6 is a disposable part of the apparatus according to the invention. The embodiment of the apparatus shown in FIG. 2 includes a control unit 15 which is intended to be reused. The disposable canister 6 is detachably arranged on the control unit. Two washers 16 and 17 are arranged to provide gastight sealing between the canister and the control unit.

The wound cover 1 comprises a wound filler 2 for instance in the form of an open-cell polymer foam and a sealing film 3 arranged over the wound filler and fastened to the skin of the patient. A soft tube 18 is arranged to connect at one end to the first conduit 8 at a connector 19. The third conduit 13 is connected to the first conduit in the connector. A check valve 20 is arranged to allow flow from the third conduit to the first conduit and hinder flow of gas and liquid in the opposite direction. The interior of the tube 18 consists of a strand 32 made of an open-pored foam material. The tube casing may consist of two plastic films made of a soft elastic plastic, which plastic films are connected along the edges of the tube to form a casing which runs around the strand 32. At one end of the tube, the plastics films have a widened portion for the formation of the fixing member 18'. One of said plastic films is at the widened portion provided with a central opening, which, when the tube is used, is intended to be placed right in front of an applied hole in the sealing film 3. Said one of the plastics film is provided with a bonding agent for connection to the outer side of the sealing film around the hole made therein. The said bonding agent is expediently constituted by a silicone adhesive, which gives good sealing and prevents leakage at the fixing member. One advantage with silicone adhesive is that the fixing member can be easily detached and refastened to the sealing film should the fixing member end up wrong on the sealing film.

Alternatively, other pressure-sensitive adhesives, such as acrylate, may be used.

A tube of the described kind is soft and pliable and can be of thin configuration. The soft tube is comfortable for the patient and does not give rise to chafes against the skin of the patient when load stresses arise.

The tube 18 can also be made as described in our application WO 2009/002260.

The first and third conduits are connected to the canister via a connector 21.

The negative pressure in the canister 6 is established with the first pump 9. An odour filter 22 with activated carbon is arranged in the canister in front of the second conduit 10 to prevent odour from reaching ambient air. In the embodiment according to FIG. 2 a further filter 23 is arranged after the first pump to further clean gas that is exhausted to ambient air. As described above the circulating pump transport an amount of air from the canister 6 through the third conduit 13 for pushing out a possible liquid column in the first conduit to the canister. As the control unit with the circulating pump will be used repeatedly by different patients a bacteria filter 24 is arranged in the third conduit for preventing that bacteria is transferred from one patient to another.

In the canister 6 is in the disclosed embodiment arranged absorbent material 25 in form of super absorbent material, such as super absorbent powder or fibers bonded to textile material or to thermoplastic fibers. Such an arrangement is advantageous when the apparatus is intended to be portable in order to prevent that liquid exudate in the canister is splashing when the patient moves. A spacer 26 is arranged to prevent that formed superabsorbent gel closes the filter 22.

An indicator, such as an optic indicator (not shown) may be arranged to indicate when the canister is filled with exudate. The canister is an airtight plastic container with a size of approximately 300 ml.

The control unit includes a rechargeable battery 27. The battery charger is marked with 28. A printed circuit board (PCB) 29, includes electronics for control of running of the pumps. An alarm buzzer 30 is connected to the PCB as well as a human machine interface (HMI) 31.

To alert the user of some undesirable situations there are arranged a few alarms in the apparatus. These alarms notifies the user when the battery level is low, if there is a leakage, if the canister is almost full or if there is a blockage somewhere in the conduits. These alarms may be a sound signal with the buzzer 30 and/or a visible sign on a display on the HMI.

The apparatus is preferably arranged so that the user is able to use the control unit in everyday life. For this purpose there are a number of requirements that regulate the time to charge the batteries, how often the batteries need to be charged, durability, noise vibrations etc. The battery should preferably last at least for twenty-four hours and the time for charging the batteries should preferably not exceed three hours.

The control unit is programmed so that the circulating pump works intermittently. Preferably the control unit is arranged such that said circulation pump is time controlled in order to control the maximal height of a possible liquid column that can be built up in the first conduit during a period when the circulating pump is turned off. The height of such a liquid column that can be built up during such a period depends of course of the amount of wound exudate that is sucked from a wound for a given period and this amount depends of course on several different factors, such as the size, the type and state of the wound.

In the apparatus means can be arranged in the PCB to analyse the power consumption of the circulating pump and provide an alarm signal when said power consumption exceeds a value that indicates that the first conduit and/or the canister is blocked.

The apparatus and method according to the invention is not limited to the above described embodiments. A number of variants are possible within the scope of the following claims.

The invention claimed is:

1. An apparatus for treating a wound with negative pressure, said apparatus comprising:
   a wound cover,
   a first pump for providing said negative pressure to the wound,
   a canister,
   a first conduit between the wound cover and the canister, which first conduit connects the wound with the canister,
   means for measuring the pressure within the canister,
   a second conduit which connects the canister with the first pump, and
   a circulating pump that is arranged to transport gas from the canister to the wound region via a third conduit and back to the canister via the first conduit in order to press out a possible liquid column from the first conduit to the canister, wherein the third conduit is positioned between the wound cover and the circulating pump.

2. The apparatus of claim 1, wherein the circulating pump is arranged to work intermittently.

3. The apparatus of claim 2, wherein said circulation pump is time controlled in order to control the maximal height of a possible liquid column that can be built up in the first conduit during a period when the circulating pump is turned off.

4. The apparatus of claim 1, wherein said means for measuring the pressure within the canister is a pressure sensor.

5. The apparatus of claim 1, wherein a check valve is arranged to hinder gas pumped by the circulating pump from reaching the wound area.

6. The apparatus of claim 5, wherein said check valve is arranged in a connecting branch on the wound cover.

7. The apparatus of claim 1, wherein said wound cover comprises a wound filler and a sealing film.

8. The apparatus of claim 7, further comprising a soft adapter which is arranged to connect the wound under the sealing film with the first conduit, and wherein said soft adapter comprises a soft, flexible tube, which is arranged to be connected to said first conduit.

9. The apparatus of claim 8, wherein said soft, flexible tube comprises an outer impermeable shell of a soft thin plastic film and an open-cell foam enclosed in said shell.

10. The apparatus of claim 1, wherein means are arranged to analyse the power consumption of the circulating pump and provide an alarm signal when said power consumption indicates that the first conduit and/or the canister is blocked.

11. An apparatus for treating a wound with negative pressure, said apparatus comprising:
 a wound cover,
 a first pump for providing said negative pressure to the wound,
 a canister,
 a first conduit between the wound cover and the canister, which first conduit connects the wound with the canister,
 means for measuring the pressure within the canister,
 a second conduit which connects the canister with the first pump, and
 a circulating pump that is arranged to transport gas from the canister to the wound region via a third conduit and back to the canister via the first conduit in order to press out a possible liquid column from the first conduit to the canister, wherein the third conduit is positioned between the wound cover and the circulating pump, wherein a first filter is arranged in the canister at an outlet to the second conduit and wherein said filter comprises activated carbon.

12. The apparatus of claim 11, wherein a second filter is arranged in the third conduit to prevent entrance of contaminated gas from the canister to the third conduit.

13. The apparatus of claim 12, wherein a third filter is arranged between the first pump and ambient air.

14. A method for controlling the negative pressure in a wound with use of an apparatus for treating wound with negative pressure, comprising:
 using a first pump to create a negative pressure within a canister, which is connected with the wound via a first conduit, and
 measuring the pressure in the canister,
 wherein gas is transported with a circulating pump from the canister towards the wound region via a third conduit that is positioned between the wound cover and the circulating pump, and wherein said gas is further directed to the first conduit and back through the first conduit to the canister for pushing a possible liquid column of wound exudate residing in the first conduit to the canister.

15. The method of claim 14, wherein the gas is pushed through the third conduit with said circulating pump at regular time intervals and that the length of said time interval is chosen for setting maximal allowed difference of the negative pressure within the wound relative to the set pressure in the canister.

16. The apparatus of claim 6, wherein the check valve is arranged in the connecting branch on the wound cover to allow the gas volume pumped by the circulating pump to reach the canister via the first conduit.

* * * * *